(12) United States Patent
Chen et al.

(10) Patent No.: US 9,750,844 B2
(45) Date of Patent: Sep. 5, 2017

(54) COMPOSITION FOR USE IN WOUND HEALING IN BURNS

(71) Applicants: ACADEMIA SINICA, Taipei (TW); NATIONAL TAIWAN OCEAN UNIVERSITY, Keelung (TW)

(72) Inventors: Jyh-Yih Chen, Yilan County (TW); Chang-Jer Wu, Taipei (TW); Han-Ning Huang, Taipei (TW)

(73) Assignees: ACADEMIA SINICA, Taipei (TW); NATIONAL TAIWAN OCEAN UNIVERSITY, Keelung (TW)

( * ) Notice: Subject to any disclaimer, the term of this patent is extended or adjusted under 35 U.S.C. 154(b) by 0 days.

(21) Appl. No.: 14/857,189

(22) Filed: Sep. 17, 2015

(65) Prior Publication Data

US 2016/0082146 A1 Mar. 24, 2016

Related U.S. Application Data

(60) Provisional application No. 62/052,031, filed on Sep. 18, 2014.

(51) Int. Cl.
*A61L 26/00* (2006.01)
*A61L 15/46* (2006.01)
*A61L 15/32* (2006.01)

(52) U.S. Cl.
CPC .......... *A61L 26/0047* (2013.01); *A61L 15/32* (2013.01); *A61L 15/325* (2013.01); *A61L 15/46* (2013.01); *A61L 26/0033* (2013.01); *A61L 26/0066* (2013.01); *A61L 2300/252* (2013.01); *A61L 2300/404* (2013.01); *A61L 2300/412* (2013.01)

(58) Field of Classification Search
None
See application file for complete search history.

(56) References Cited

U.S. PATENT DOCUMENTS

2010/0184647 A1* 7/2010 Chen .................. A61K 38/1767
514/2.4

FOREIGN PATENT DOCUMENTS

WO WO 2010/079342 A2 * 7/2010

OTHER PUBLICATIONS

Huang et al. ("Use of the antimicrobial peptide Epinecidin-1 to protect against MRSA infection in mice with skin injuries," Biomaterials, 2013, vol. 34, pp. 10319-10327).*
Cook ("Methicillin-resistant *Staphylococcus aureus* versus the burn patient," Burns 1998, vol. 24, pp. 91-98).*
Capoor et al. ("Fungal infections in burns: Diagnosis and management," Indian J Plast Surg. 2010, vol. 43, pp. S37-S42).*

* cited by examiner

*Primary Examiner* — Christina Bradley
(74) *Attorney, Agent, or Firm* — Birch, Stewart, Kolasch & Birch, LLP

(57) ABSTRACT

The preset invention relates to a new method for wound healing, particularly in burns, comprising Epinecidin-1 (Epi-1) or Pardaxin (GE33), optionally in the incorporation into collagen.

2 Claims, 15 Drawing Sheets

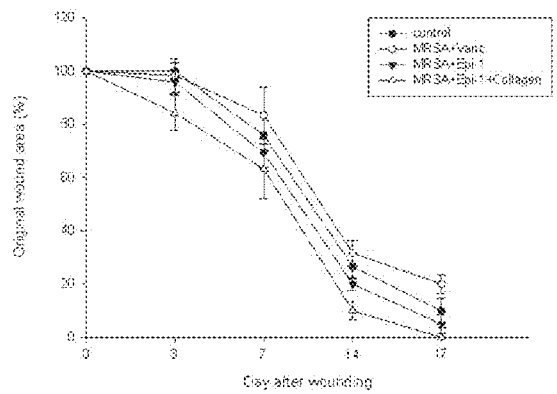
Figure 3A
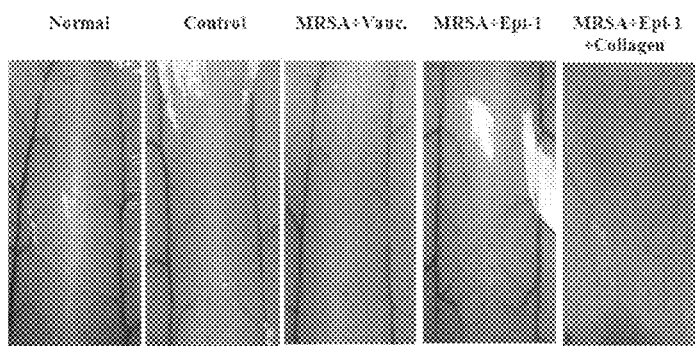
Figure 3B
| Organism | Condition | Day | Bacterial Count |
|---|---|---|---|
| MRSA | MRSA | 0 | 5.52x10³ CFU/10 ml |
| | | 3 | 8.1x10⁹ CFU/10 ml |
| | | 7 | Fatal |
| | | 14 | Fatal |
| | | 17 | Fatal |
| | MRSA+Vanc. | 0 | 5.4x10⁴ CFU/10 ml |
| | | 3 | 2x10⁹ CFU/10 ml |
| | | 7 | 3.42x10⁴ CFU/10 ml |
| | | 14 | 2x10² CFU/10 ml |
| | | 17 | 67 CFU/g |
| | MRSA+Epi-1 | 0 | 5.11x10⁴ CFU/10 ml |
| | | 3 | 1.12x10⁶ CFU/10 ml |
| | | 7 | 2.02x10³ CFU/10 ml |
| | | 14 | 50 CFU/10 ml |
| | | 17 | 22 CFU/g |
| | MRSA+Epi-1+collagen | 0 | 5.4x10⁴ CFU/10 ml |
| | | 3 | 2x10⁶ CFU/10 ml |
| | | 7 | 2.32x10³ CFU/10 ml |
| | | 14 | 21 CFU/10 ml |
| | | 17 | 15 CFU/g |
Figure 3C

COMPOSITION FOR USE IN WOUND HEALING IN BURNS

RELATED APPLICATIONS

This application claims the benefit of U.S. provisional application No. 62/052,031, filed Sep. 18, 2015 under 35 U.S.C. §119, the entire content of which is incorporated herein by reference.

FIELD OF THE INVENTION

The present invention relates to a new method or composition for wound healing, particularly in burns.

BACKGROUND OF THE INVENTION

The discovery of antibiotics has been one of the greatest achievements of modern medicine, but their excessive use has selected for resistant bacteria. Cases of infection due to multiply resistant organisms, such as methicillin-resistant *Staphylococcus aureus* (MRSA) and vancomycin-resistant Enterococcus (VRE), continue to increase. At the same time, there has been a decline in the development of new antibacterial therapies.

Antimicrobial peptides (AMPs), in place of antibiotics, act as the first line of defense against invading pathogens, and also help to modulate host immune responses. One of the AMPs, Epinecidin (Epi)-1, is a 21-amino-acid peptide that was first identified in a fish species, grouper (*Epinephelus coioides*) [Pan et al., Gene expression and localization of the epinecidin-1 antimicrobial peptide in the grouper (*Epinephelus coioides*), and its role in protecting fish against pathogenic infection. DNA Cell Biol 2007, 26:403-13; or Taiwan Patent No. I-299335.] Structurally, the peptide is similar to pleurocidin, a protein of the winter flounder (*Pleuronectes americanus*). Synthetic Epi-1 exerted immunomodulatory and protective effects against infection with Gram negative bacteria in several hosts, including *Pseudomonas aeruginosa* infection in mice, *Vibrio vulnificus* infection in zebrafish, and *Riemerella anatipestifer* infection in duck [Lin et al., Epinecidin-1, an antimicrobial peptide from fish (*Epinephelus coioides*) which has an antitumor effect like lytic peptides in human fibrosarcoma cells. Peptides 2009, 30:283-90; Lee et al., The antimicrobial peptide, epinecidin-1, mediates secretion of cytokines in the immune response to bacterial infection in mice. Peptides 2012, 36:100-8; Pan et al., Insights into the antibacterial and immunomodulatory functions of the antimicrobial peptide, epinecidin-1, against *Vibrio vulnificus* infection in zebrafish. Fish Shellfish Immunol 2011, 31:1019-25; Pan et al., Antimicrobial peptides of an anti-lipopolysaccharide factor, epinecidin-1, and hepcidin reduce the lethality of Riemerella anatipestifer sepsis in ducks. Peptides 2010, 31:806-15]. It was also confirmed that oral administration of recombinant Epi-1 protected grouper (*Epinephelus coioides*) and zebrafish (*Danio rerio*) from Gram negative *Vibrio vulnificus* infection [Pan et al., Oral administration of recombinant epinecidin-1 protected grouper (*Epinephelus coioides*) and zebrafish (*Danio rerio*) from *Vibrio vulnificus* infection and enhanced immune-related gene expressions. Fish Shellfish Immunol 2012, 32:947-57.] Epi-1 also exhibited antibacterial activity against Gram positive strains, as well as antifungal and antiviral activity [Pan et al., In vitro activities of three synthetic peptides derived from epinecidin-1 and an anti-lipopolysaccharide factor against Propionibacterium acnes, Candida albicans, and Trichomonas vaginalis. Peptides 2009, 30:1058-68; Wang et al., Inactivation of nervous necrosis virus infecting grouper (*Epinephelus coioides*) by epinecidin-1 and hepcidin 1-5 antimicrobial peptides, and downregulation of Mx2 and Mx3 gene expressions. Fish Shellfish Immunol 2010, 28:113-20; Pan et al., Evaluation of the epinecidin-1 peptide as an active ingredient in cleaning solutions against pathogens. Peptides 2010; 31:1449-58]. Moreover, Epi-1 was reported to promote resistance to bacterial infections by stabilizing the cytoskeleton network in host cells [Huang and Chen, Proteomic and functional analysis of zebrafish after administration of antimicrobial peptide epinecidin-1. Fish Shellfish Immunol 2013, 34:593-8].

Pardaxin is also known as GE33, as it is a 33 amino acid peptide that starts with glycine (G) and ends with glutamic acid (E) [Oren and Shai, A class of highly potent antibacterial peptides derived from pardaxin, a pore-forming peptide isolated from Moses sole fish Pardachirus marmoratus. *Eur J Biochem* 1996, 237: 303-10, or U.S. Pat. No. 6,172,038]. GE33 is a pore forming peptide with an a-helix structure, which confers selective cytolytic activity against bacteria [Oren et al., A repertoire of novel antibacterial diastereomeric peptides with selective cytolytic activity. *J Biol Chem* 1997, 272: 14643-9]. GE33 was reported to have antimicrobial activity against both Gram-positive and -negative bacteria. Furthermore, clinical case studies have shown that application of GE33 to severely infected cutaneous wounds can clear the infection and improve healing. Thus, GE33 has many features consistent with antibiotics, but potentially has broader applications, and may avoid or reduce concerns of bacterial resistance [Hsu et al., Pardaxin-induced apoptosis enhances antitumor activity in HeLa cells. *Peptides* 2011, 32: 1110-6; Huang et al., Pardaxin, an antimicrobial peptide, triggers caspase-dependent and ROS-mediated apoptosis in HT-1080 cells. *Mar Drugs* 2011; 9: 1995-2009; Shai and Oren, Diastereoisomers of cytolysins, a novel class of potent antibacterial peptides. *J Biol Chem* 1996; 271: 7305-8].

Methicillin-resistant *Staphylococcus aureus* (MRSA) is a major cause of infection in injured patients, and healthcare associated (HA) and community associated (CA) MRSA have become prevalent in recent years. Its emergence is a consequence of excessive use of certain antibiotics. MRSA generally does not cause infection in the absence of injury. When MRSA enters the body through a cut or abrasion, it may cause infection by evading the natural protective mechanisms of the body. This necessitates the use of alternative therapies, which ideally do not result in resistance through continuous selective pressure. MRSA infections in recent years have been treated with mupirocin, clindamycin, trimethoprim/sulfamethoxazole, doxycycline, minocycline, linezolid, vancomycin, daptomycin, and telavancin [Bjorn et al., Anti-infectious and anti-inflammatory effects of peptide fragments sequentially derived from the antimicrobial peptide centrocin 1 isolated from the green sea urchin, *Strongylocentrotus droebachiensis*. AMB Express 2012, 2:67]. Also, vancomycin, linezolid, daptomycin (Cubicin), tigecycline (Tygacil), and telavancin (Vibativ) were reported to treat severe MRSA infections of skin and soft tissue in hospitals. Vancomycin, the primary treatment for MRSA, possesses high minimum inhibitory concentration (MIC) values and other limitations [Palazzolo-Ballance et al., Neutrophil microbicides induce a pathogen survival response in community-associated methicillin-resistant *Staphylococcus aureus*. J Immunol 2008, 180:500-9]. Induction of AMP (e.g., cathelicidin) release in response to cutaneous skin injury has been documented; however, the effect of AMPs on MRSA infection has been incompletely studied [Dorschner et al., Cutaneous injury induces the release of cathelicidin anti-microbial peptides active against group A Streptococcus. J Invest Dermatol 2001, 117:91-7.27]. Accordingly, there is no way to confirm which of AMPs is effective in wound healing, particularly in burns.

SUMMARY OF THE INVENTION

It is unexpectedly found that Epinecidin-1 (Epi-1) is effective in wound healing. Accordingly, the present invention provides a new method for wound healing, particularly in Burns. In one embodiment of the invention, the method comprises the use of Epinecidin-1 (Epi-1) or Pardaxin (GE33), optionally in the incorporation into collagen.

In one aspect, the invention provides a method for wound healing comprising applying to the wound in a subject in need thereof, a composition comprising Epinecidin-1 (Epi-1) or Pardaxin (GE33), together with a pharmaceutically acceptable carrier. In one particular example of the invention, the method is effective in treatment for burns.

In another aspect, the invention provide a method for wound healing, particularly in burns, comprising applying to the wound in a subject in need thereof, a composition comprising Epi-1 or GE33, in the incorporation into collagen, together with a pharmaceutically acceptable carrier.

In one yet aspect, the invention provides a pharmaceutical composition for wound healing in burns, comprising Epi-1 or GE33, in the incorporation into collagen, together with a pharmaceutically acceptable carrier.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment which is presently preferred. It should be understood, however, that the invention is not limited to this embodiment.

In the drawings:

FIGS. 3A-3B show that Epi-1 enhances wound healing and angiogenesis, and decreases bacterial counts in MRSA infected mice. A skin region of about 1 square centimeter was removed from the abdomen of non-anaesthetized mice, and the wound was infected with 50 µl of broth mix containing $10^6$ cfu of MRSA alone, or together with vancomycin, Epi-1, or Epi-1 and collagen. Wound areas at 3, 7, and 14 days after infection were shown in FIG. 3A. FIG. 3B provides photographs showing the formation of blood vessels in wounded skin in the indicated treatment groups in F. In FIG. 3C, skin sections from the indicated days were cultured, and bacterial counts shown as colony forming units (CFU).

FIG. 8A shows that all full thickness aseptic wounds closed by Day 25. FIG. 8B shows that the full thickness wounds contaminated with a mixture of microorganisms increased in size initially, while GE33-treated wounds did not exhibit the initial expansion and closed somewhat faster (Day 21) than vancomycin-treated wounds. FIG. 8C provides photographs of the representative wounds, wherein 'fatal' indicates that no mice survived. FIG. 8D shows the data of bacterial load, containing the average of four mice at each time point; control refers to initial inocula for each mouse.

FIG. 9A shows that the wound biopsies of infected mice (untreated controls or mice treated with the indicated antibiotic or GE33/collagen) were Gram stained at Day 3, wherein gram-positive microorganisms are indicated by violet rods. Gram-positive microorganisms were reduced in mice treated with GE33, as compared to the untreated group (arrows indicate bacterial clusters in the tissue; and images are representatives of the two experiments, each performed in triplicate). FIG. 9B provides the results of the evaluation of the dermal and epidermal maturation (magnification: ×100; the length and height of the photomicrographs: 500 μm).

FIG. 10B provides the representative skin histopathology of Balb/c mice at Day 3 following inoculation of wounds with MRSA (Giemsa stain, original magnification, ×100).

DETAILED DESCRIPTION OF THE INVENTION

Figure 1A:
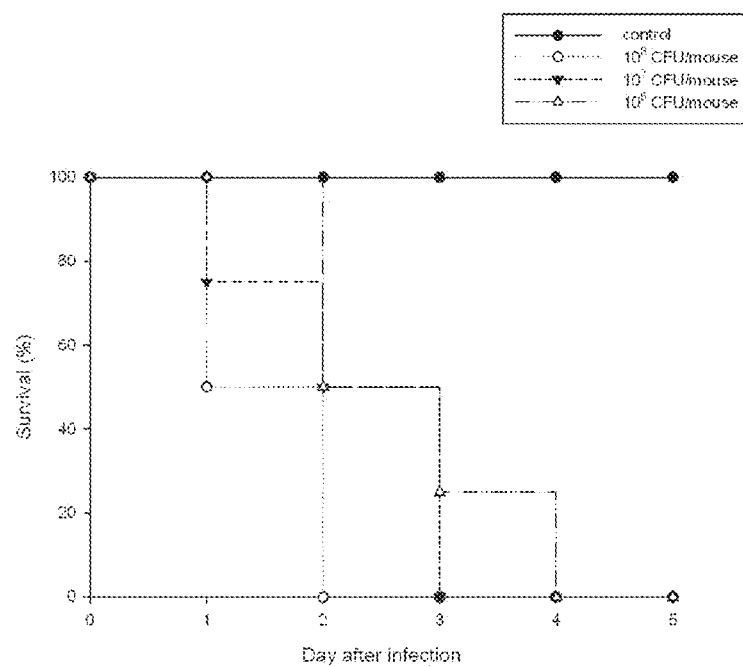
FIGS. 1A-1B show the MRSA infection of wounds causing mortality in mice; wherein a skin region of about 1 square centimeter was removed from the abdomen of non-anaesthetized mice, and the wound was infected with 50 µl of broth mix containing the indicated cfu of MRSA, the survival of mice on a daily basis was shown in FIG. 1A, and FIG. 1B provides photographs showing wound regions at 3, 7, and 14 days after infection with $10^6$ cfu of MRSA, wherein 'fatal' denotes that no mice survived after the treatment.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

As used herein, the term "Epinecidin-1" or "Epi-1" is refer to an Epinecidin peptide or a derivate, fragment or variant thereof. One example is Epicidine-1 refers to a 21-amino acid peptide, which was first identified in a fish species, grouper (*Epinephelus coioides*) as provided in Pan et al. [DNA Cell Biol 2007, 26:403-13; or Taiwan Patent No. I-299335], which has the amino acid sequence below:

(SEQ ID NO: 1)
Gly-Phe-Ile-Phe-His-Ile-Ile-Lys-Gly-Leu-Phe-His-
Ala-Gly-Lys-Met-Ile-His-Gly-Leu-Val.

Examples of Epi-1 include but are not limited to all Epicidine-1 pepetides, derivate, fragment or variant thereof as shown in Taiwan Patent No. I-299335.

The term "a functional derivate, fragment or variant thereof" as used herein refers to a derivate, fragment or variant of the peptide that maintains same or similar activity, and exhibits same or similar properties.

As used herein, the term "Pardaxin" or "GE33" refers to a Pardaxin peptide or a derivate, fragment or variant thereof. One preferable example of Pardaxin refers to a peptide having 33 amino acids that starts with glycine (G) and ends with glutamic acid (E), as described in Oren and Shai [*Eur J Biochem* 1996, 237: 303-10, or U.S. Pat. No. 6,172,038], which has the amino acid sequence below:

(SEQ ID NO: 2)
Gly-Phe-Phe-Ala-Leu-Ile-Pro-Lys-Ile-Ile-Ser-Ser-
Pro-Leu-Phe-Lys-Thr-Leu-Leu-Ser-Ala-Val-Gly-Ser-
Ala-Leu-Ser-Ser-Ser-Gly-Gly-Gln-Glu.

Examples of Pardaxin include but are not limited to all Pardaxin pepetides, derivate, fragment or variant thereof as shown in U.S. Pat. No. 6,172,038.

It was confirmed in Examples 1-4 that Epi-1 is a potential complementary treatment to the use of antibiotics based on the findings: (i) the use of peptides like Epi-1 was unlikely to induce resistance, as AMPs did not have direct effects on microbes; (ii) Epi-1 is compatible for use with antibiotics, and does not have any apparent immunotoxic effects; (iii) Epi-1 were found to have prophylactic efficacy, and inability to engender resistance, which supports that Epi-1 is suitable for use in cases with a high risk of infection; and (iv) in closing, topical application of Epi-1 was effective in the treatment of MRSA infection, and the wound healing was accelerated upon the incorporation into collagen.

It was also evidenced in Examples 5-7 that GE33 may complement the use of GE33 based on the findings: (i) GE33 did not induce resistance, as they do not have direct effects on microbes; (ii) GE33 could selectively modulate innate immune responses, thereby providing prophylaxis or treatment of a broad spectrum of infections, while balancing or controlling the attendant inflammatory response; (iii) GE33 increased macrophage and monocyte recruitment; and (iv) GE33 also stimulated a variety of signaling pathways, which induced key chemokines It is also demonstrated in the examples, Epi-1 or GE33 ameliorates excess recruitment of monocytes and macrophage cells, and increase VEGF expression, and decreased induction of MCP-1, IL-6, and TNF.

Accordingly, the invention provides a method for wound healing comprising applying to the wound in a subject in need thereof, a composition comprising Epinecidin-1 (Epi-1) or Pardaxin (GE33), together with a pharmaceutically acceptable carrier.

On the other hand, the invention provides a use of a composition in manufacturing a medicament for wound healing, wherein the composition comprises Epi-1 or GE33, together with a pharmaceutically acceptable carrier.

In one particular example of the invention, Epi-1 or GE33 is effective in treatment for wound healing in burns.

In addition, the invention provides a composition in manufacturing a medicament for wound healing, wherein the composition comprises Epi-1 or GE33, together with a pharmaceutically acceptable carrier.

It is also found that Epi-1 or GE33 the incorporation into collagen provides improved effect in wound healing, particularly in burns.

Accordingly, the invention provides a method for wound healing using Epi-1 or GE33 in the incorporation into collagen; and a use of a composition in manufacturing a medicament for wound healing, particularly in burns, wherein the composition comprises Epi-1 or GE33 in the incorporation into collagen, together with a pharmaceutically acceptable carrier.

Furthermore, the invention provides a pharmaceutical composition for wound healing, particularly in burns, comprising Epi-1 or GE33, in the incorporation into collagen, together with a pharmaceutically acceptable carrier.

In the invention, the pharmaceutical composition may be formulated using any standard technology or commonly used methods known to those skilled in the art.

The term "therapeutically effective amount" as used herein refers to an amount of a drug or pharmaceutical agent which, as compared to a corresponding subject who has not received such amount, results in an effect in treatment or healing of a disease, disorder, or side effect, or a decrease in the rate of advancement of a disease or disorder. The term also includes within its scope amounts effective to enhance normal physiological function.

For use in therapy, therapeutically effective amounts of the peptide, or functional variant thereof, may be formulated as a pharmaceutical composition for administration. Accordingly, the invention further provides a pharmaceutical composition comprising a therapeutically effective amount of the peptide or a functional derivate, fragment or variant thereof, together with one or more pharmaceutically acceptable carriers.

The term "a pharmaceutically acceptable carrier" as used herein refers to a carrier, diluent, or excipient that is pharmaceutically acceptable, in the sense of being compatible with the other ingredients of the formulation and not deleterious to the subject to be administered with the pharmaceutical composition. Any carrier, diluent or excipient commonly known or used in the field may be used in the invention, depending to the requirements of the pharmaceutical formulation.

According to the invention, the pharmaceutical composition may be adapted for administration by any appropriate route, including but not limited to topical, rectal, nasal, vaginal, oral or parenteral route. In one particular example of the invention, the pharmaceutical composition is formulated for topical administration. Such formulations may be prepared by any method known in the art of pharmacy. One example of the invention is a pharmaceutical composition in the form of a cover, a deposit, or a pad.

The present invention will now be described more specifically with reference to the following examples, which are provided for the purpose of demonstration rather than limitation.

EXAMPLES

Materials and Methods

Mice and Bacterial Culture

Six to eight week old Balb/C male mice were used for the examples. MRSA culture and quantification were carried out, and suspensions were serially diluted and spread onto LB-agar plates in duplicate for 24 hours. After the incubation period, colony forming units (CFU) were counted, averaged, and expressed as CFU/ml. All animal handing procedures were in accordance with National Taiwan Ocean University (NTOU) guidelines. All procedures were approved by the Animal Care and Use Committee of NTOU.

The murine macrophage cell line J774A.1 (ATCC, collection TIB-67) was maintained in RPMI 1640 containing 10% fetal bovine serum and 1% penicillin/streptomycin (complete media; Life Technologies, Grand Island, New York). J774A.1 cells were cultured at $1 \times 10^4$ cells/mL at 37° C. in a humidified incubator with 5% $CO_2$.

Reagents

Elisa kits for MCPJ (Cat no. 555260, BD Biosciences, CA, USA), IL-6 (Cat no. 555240, BD Biosciences, CA, USA), and TNF (Cat no. 558534, BD Biosciences, CA, USA) were used to determine cytokine levels. Antibodies against macrophages (Cat no. 550282, BD Biosciences, CA, USA), monocytes (Cat no. 101301, BioLegend, London, UK), and VEGF (Cat no. 550549, BD Biosciences, CA, USA) were used for immunohistochemistry (IHC). Fish scale collagen peptides (FSCPs) were isolated from tilapia (*Oreochromis* sp.) by the Seafood Technology Division, Fisheries Research Institute, Council of Agriculture, Taiwan.

Statistical Analysis

All experiments were performed in triplicate, on three biological replicates. Error bars represent the standard deviation, and significant differences between groups ($p=0.05$) were determined using ANOVA. Different letters above the bar were used to indicate significant differences between groups. Groups of four mice were used for in vivo analysis; each in vivo experiment was repeated at least twice.

Induction of Inflammatory Trauma in Mice by Skin Excision

The mice were housed individually to prevent fighting and further damage to the wounds, and were given ad libitum access to food and water. The mice were maintained under 12 h/12 h light/dark cycle at a room temperature, and adapted to the environment for at least a week before used in the experiments. Each mouse's hair was removed from the back by shaving, and a full-thickness excisional wound (1 cm in diameter) was created on the back of the mice.

Each wound was inoculated with 50 µl of broth mix containing $10^6$ CFU of the indicated microorganism. The wounds were treated with the antimicrobial peptide according to the invention and collagen at 5 min after inoculation. At 30 min after treatment, wounds were covered with Tegaderm to maintain uniformity and to prevent the loss of the materials as treated. The wounds were examined at Day 3, 7, and 14 after the wounds were created, and the non-contaminated wounds were examined every other day. The wounds were examined to assess the transitions from inflammatory to regenerative and regenerative to resolving phases of the wound healing. At the end of the examination period, the animals were euthanized by $CO_2$ inhalation and the wounds were assessed. For each experiment, four individuals were examined in each group at each time point. Each wound was measured and then removed from the animal, with unwounded skin taken from the contralateral abdomen as a control.

Assessment of Wound Infection

Tissue samples were homogenized in PBS. Serially diluted aliquots of homogenate were cultured on Luria-Bertani agar after incubation for 18 h at 37° C., and cfu/g tissue were subsequently calculated. A stable wound infection was defined as $10^6$ cfu/g tissue.

Histological Examination

Full-thickness tissue was harvested for microbial and histological analysis. Samples from each experiment were fixed in 4% buffered paraformaldehyde. Tissue samples were stained with hematoxylin/eosin or Giemsa, and immunohistochemistry (IHC) was analyzed by three independent investigators. Images were taken with a BX-51 microscope (Olympus, Japan).

Wound Closure Measurements

Tracings were taken immediately after injury. For uncontaminated wounds, wound size was determined every second day. For contaminated wounds, mice were euthanized at Day 3, 7, 14, or 17, and tracings of the wound edges were made. Wound areas were determined using the Macintosh Adobe Photoshop program and histological examination. The percentage of wound contraction was calculated as follows:

% Wound contraction=$(A_0-A_t)/A_0 \times 100\%$ where $A_0$ is the area of the original wound, and $A_t$ is the area of the wound on Day 3, 7, 14, and 17.

Microbial Inoculation

Multidrug-resistant strains of Staphylococcus aureus (MRSA) commonly associated with human wound infections were selected to generate a polymicrobial solution. The initial inoculum was prepared by culturing aerobic bacteria in Tryptic Soy Broth (TSB) overnight at 37° C. Broths were subsequently centrifuged at 1000 rpm for 15 min, and resuspended in TSB with 15% glycerol, or chopped meat extract with 15% glycerol (for aerobic bacteria). The concentration was adjusted to $10^6$ cfu/50 µl, and stored at $-80°$ C. Prior to wound application, the bacterial stocks were re-mixed. Microbial load was determined by direct plating, followed by freeze-thaw and cfu enumeration, in parallel with inoculations. The inoculum was delivered by sterile pipettes to the center of open wounds. After euthanization (at Day 0, 3, 7, 14, or 17), two bisected tissue segments were used to determine microbial load using the protocol for human wound biopsy culture, as stated in the UPMC Clinical Microbiology Laboratory Procedure Manual. Tissue biopsies were weighed and placed in 1.5 ml of TSB, and then homogenized in a tissue grinder. A single drop of the homogenate was placed on the slide and Gram stained for rough assessment (if one or more bacteria are present within the oil immersion field, the expected count in the tissue is at least $10^5$ cfu/g). Serial dilutions (1:10 (0.1+0.9)) of the tissue homogenate were made using distilled water. The cfu/g of tissue was calculated as follows: cfu/g=plate count (1/dilution)×10/wt. of homogenized tissue.

Example 1

Antimicrobial Effect of Epi-1 In Vitro

Minimum inhibitory concentration (MIC) and minimum bactericidal concentration (MBC) antimicrobial assays were performed. For MIC assessment, the antimicrobial peptide, Epi-1, was diluted to final concentrations of 100, 50, 25, 12.5, 6.26, 3.125, 1.582, or 0.78 µg/ml. Twenty microliters of each dilution were mixed in a microtiter plate well with 20 pl of the appropriate bacterial indicator suspension, and 160 µl of Trypticase Soy Broth (TSB) for S. aureus, to a total volume of 200 µl. Three replicates were examined for each S. aureus strain, compound, and concentration. Positive controls contained water instead of compounds, and negative controls contained compounds without bacterial suspensions. Microbial growth was automatically determined by optical density measurement at 600 nm (Bioscreen C, Labsystem, Helsinki, Finland). Microplates were incubated at 25° C. for plant pathogens and at 37° C. for food-borne bacterial strains. Absorbance readings were taken at hourly intervals over a 48 h period. Plates were shaken for 20 seconds before each measurement. The experiment was repeated twice. The lowest concentration that resulted in zero growth by the end of the experiment was taken as the MIC.

Figure 1B:
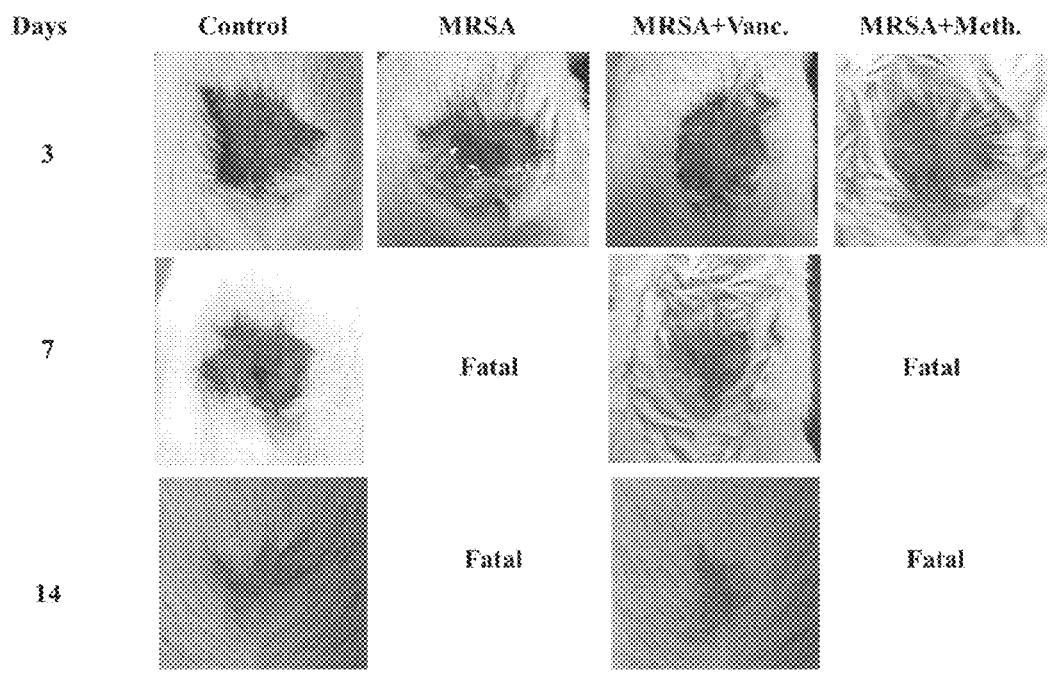

To determine the MRSA doses that cause mortality in a murine model of traumatic skin injury, the following procedures were carried out. On the back of each mice, a region of skin was excised, and the wound was infected with different CFU counts of MRSA in a 50 µl suspension. The survival of infected mice was monitored on a daily basis. All mice that received $10^8$, $10^7$, or $10^6$ CFU died by two, three, or four days respectively, while unexposed mice exhibited no mortality (FIG. 1A). Based on these observations, $10^6$ CFU of MRSA were used in subsequent experiments. To confirm that the MRSA strain possessed methicillin resistance, wounds were treated with MRSA alone or together with methicillin or commercially available vancomycin. Mice treated with MRSA alone or MRSA and methicillin died within four days, while the control group (uninfected) and mice treated with MRSA together with vancomycin survived, with re-epithelialization observed in the excision region (FIG. 1B). This confirmed the methicillin resistance of MRSA used in the present study.

Figure 2A:
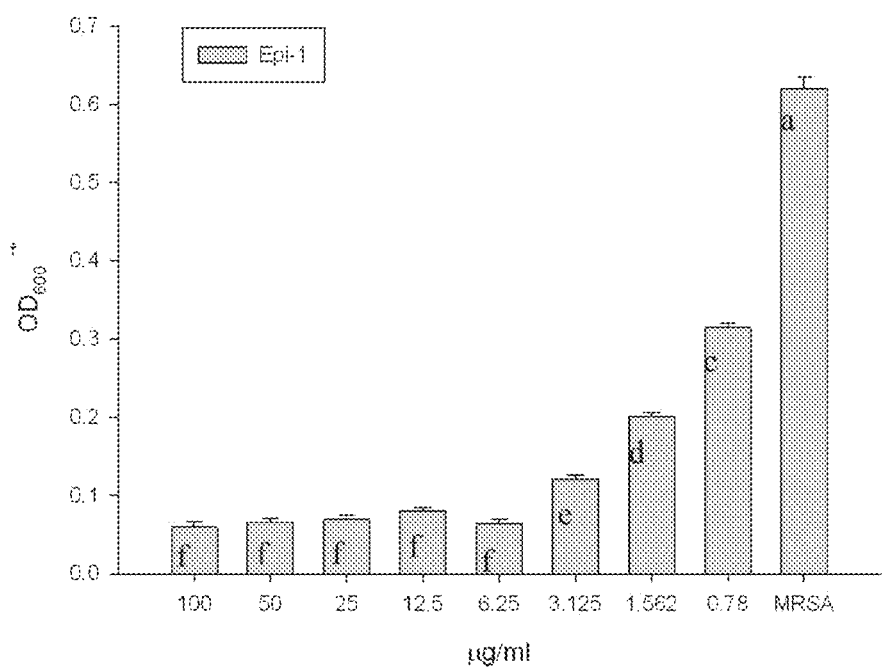
FIGS. 2A-2B provide the in vitro antibacterial activity and in vivo wound healing activity of Epinecidin-1; wherein MRSA was cultured in different concentrations of Epi-1 and relative bacterial proliferation was determined based on optical density at 600 nm, a skin region of about 1 square centimeter was removed from the abdomen of non-anaesthetized mice, and the wound was infected with 50 µl of broth mix containing $10^6$ cfu of MRSA alone, or together with Epi-1 or Epi-1 with collagen. The results were shown in FIG. 2A, and FIG. 2B provides photographs showing the wound region at 3, 7, and 14 days after infection.
Figure 2B:
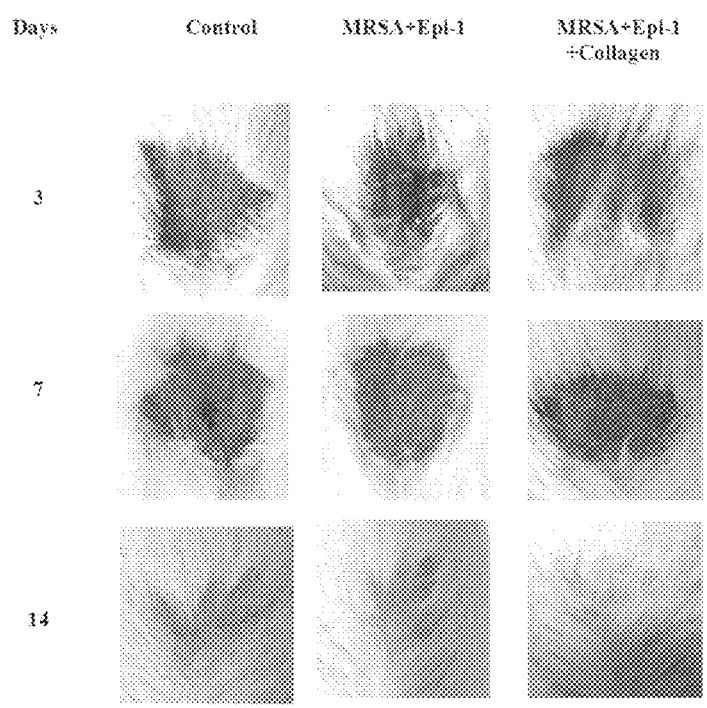

To test the effectiveness of Epi-1 against MRSA infection, the MIC and MBC of Epi-1 were carried out. As shown in FIG. 2A, Epi-1 had good antibacterial efficacy against MRSA. It was shown in FIG. 2B that the co-treatment of MRSA-infected excision wounds with Epi-1 and collagen enhanced healing and re-epithelialization as compared to Epi-1 treatment alone. After skin excision, the area of the wounded region was measured daily in uninfected mice (as a control), and infected mice treated with vancomycin, Epi-1, or Epi-1 and collagen-1; the size of the healed area was compared to that of the initial wound to assess wound closure efficiency. As shown in FIG. 3A, the wound closure was faster in mice treated with Epi-1 and Epi-1 and collagen as compared to vancomycin-treated mice and control mice. During recovery from injury, angiogenesis occurs to supply blood to the wounded region. Angiogenesis efficiency was compared between the various treatment groups under light microscopy. As shown in FIG. 3B, new blood vessel formation was more prominent in the presence of Epi-1 than vancomycin in infected mice; and as shown in FIG. 3C, the bacterial counts were also significantly lower in infected mice treated with Epi-1 than mice treated with vancomycin.

Example 2

Antibacterial Activity of Epi-1 In Vivo

Figure 4:
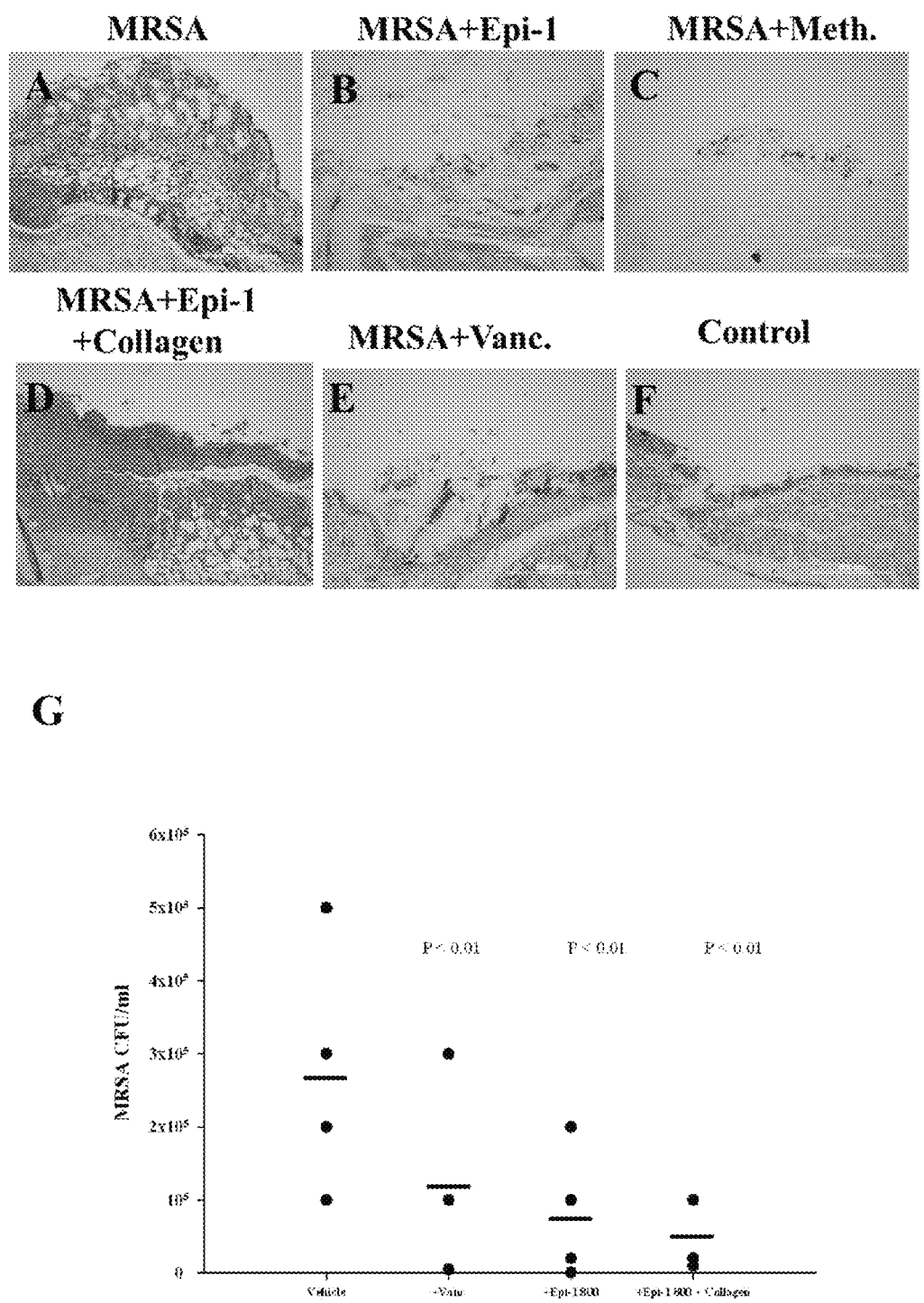
FIG. 4 shows that Epi-1 abolished MRSA in the infected area; wherein a skin region of about 1 square centimeter was removed from the abdomen of non-anaesthetized mice, and the wound was infected with 50 µl of broth mix containing $10^6$ cfu of MRSA alone, or together with methicillin, vancomycin, Epi-1, or Epi-1 and collagen as shown in FIG. 4A-4F. At Day 3 after the inoculation, tissue sections from the indicated treatment groups were subjected to Gram staining The MRSA CFUs in infected mice at 24h after treatment with the indicated compounds were shown in FIG. 4G.

To gain further insight into the efficiency of Epi-1, sections from the wounded region were subjected to Gram staining The purple staining of Gram positive MRSA (see FIG. 4A) was completely abolished in infected mice treated with methicillin, Epi-1, or Epi-1 and collagen (FIG. 4B-4D). Furthermore, Epi-1 was more efficient at attenuating MRSA infection than vancomycin (FIG. 4E). Injured skin sections were subsequently cultured, and the CFU of MRSA were calculated. Consistent with the Gram staining observations, MRSA CFU were significantly reduced in response to treatment with Epi-1, as compared to the control (FIG. 4G).

Example 3

Pro-Inflammatory Cytokine Expression of Epi-1

Figure 5A:
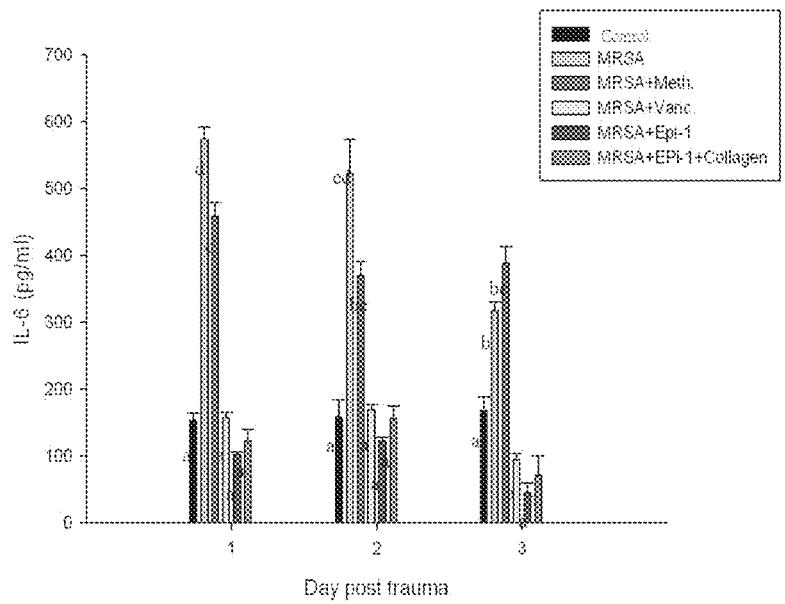
FIGS. 5A-5C show that Epi-1 modulated MRSA mediated-induction of TNF-a, IL-6, and MCP-1; wherein a skin region of about 1 square centimeter was removed from the abdomen of non-anaesthetized mice, and the wound was infected with 50 µl of broth mix containing $10^6$ cfu of MRSA alone, or together with methicillin, vancomycin, Epi-1, or Epi-1 with collagen; and at 24 h post-treatment, (A) IL-6, (B) TNF-α, and (C) MCP-1 were detected in serum by ELISA.
Figure 5B:
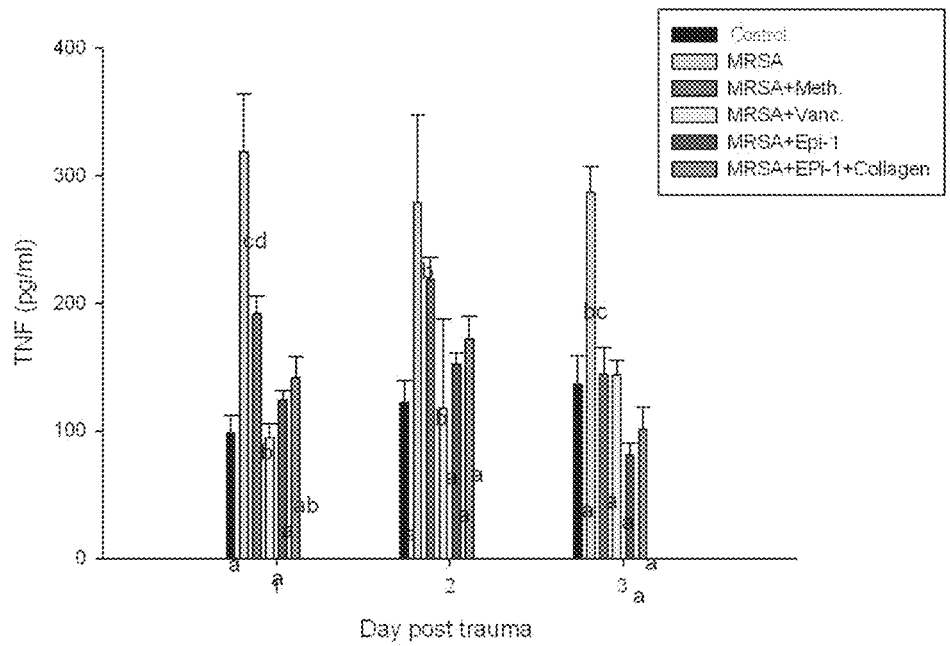
Figure 5C:
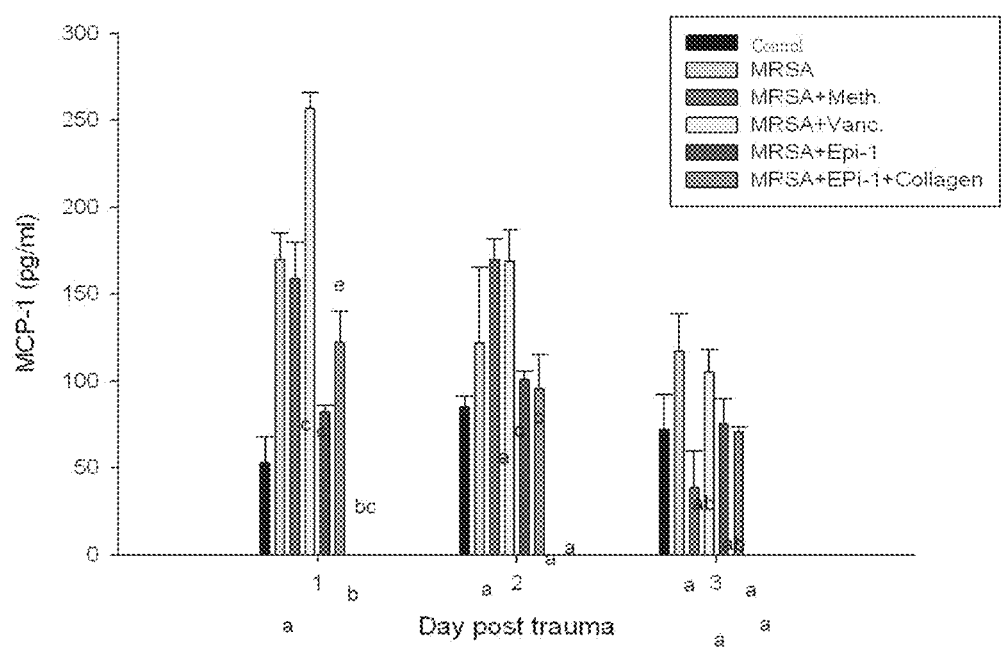

As Epi-1 had an effect against MRSA infection as shown in the previous examples, the effect of Epi-1 on the immune response to MRSA was examined. MRSA infection resulted in strong induction of TNF-α and IL-6 at 1, 2, and 3 days post-infection, and this was unaffected by methicillin treatment; however, treatment with vancomycin or Epi-1 (in the presence or absence of collagen) significantly decreased induction of IL-6 and TNF-α (FIGS. 5A and 5B). The chemoattractant MCP-1 is involved in the recruitment of monocytes to the site of injury, and helps proteins traffic across the endothelial barrier during wound healing. MCP-1 induction by MRSA was decreased by Epi-1, but not vancomycin (FIG. 5C).

Example 4

Chemotaxis and Histology of Excised Tissue after the Epi-1 Treatment

Figure 6:
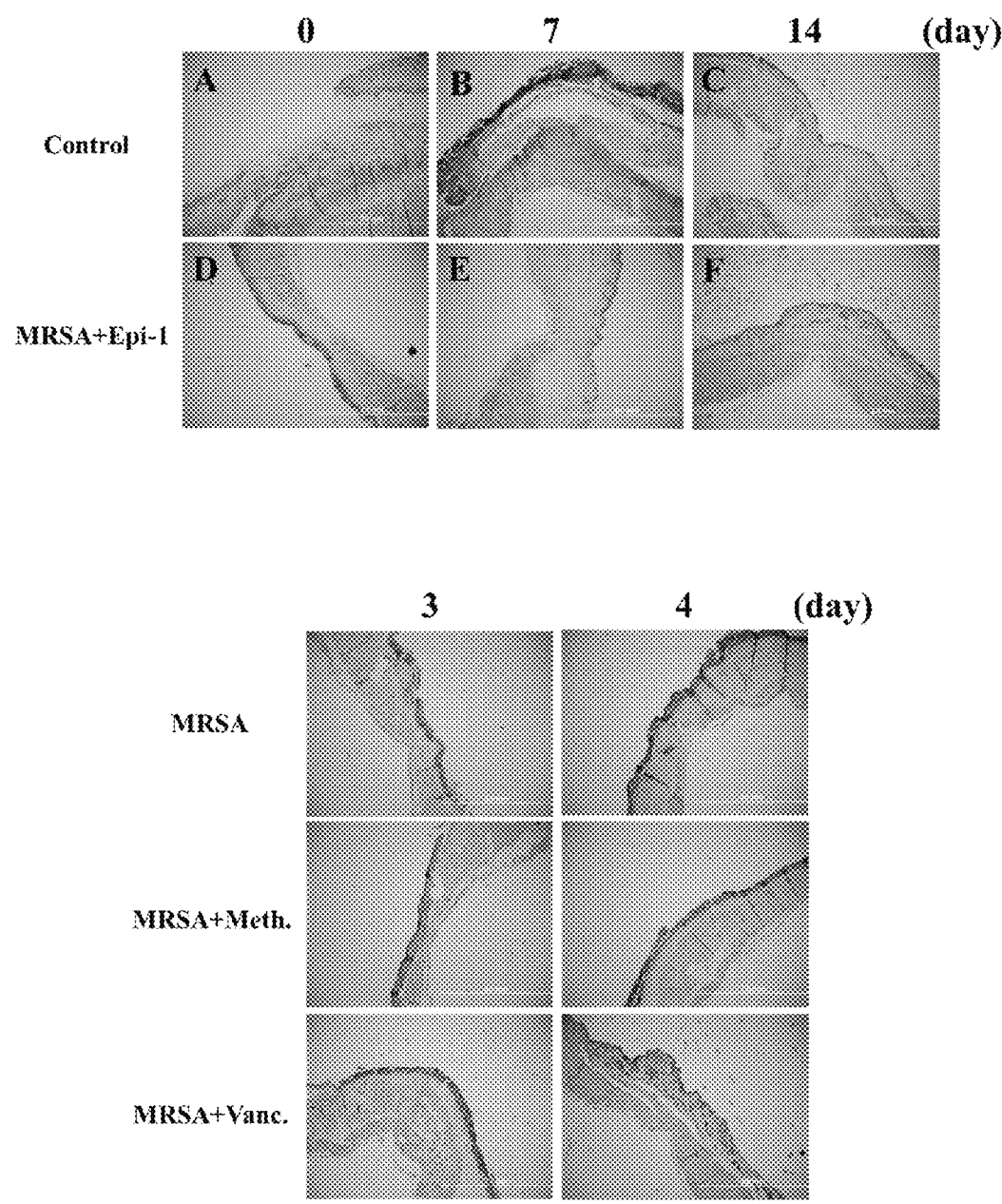
FIG. 6 show that Epi-1 regulated the accumulation of erythrocytes and platelets in infected wounds; wherein a skin region of about 1 square centimeter was removed from the abdomen of non-anaesthetized mice, and the wound was infected with 50 µl of broth mix containing $10^6$ cfu of MRSA alone, or together with methicillin, vancomycin, or Epi-1 Skin samples from the injured area were fixed and subjected to Giemsa staining at 0, 3, 4, 7, and 14 days post-treatment.
Figure 7:
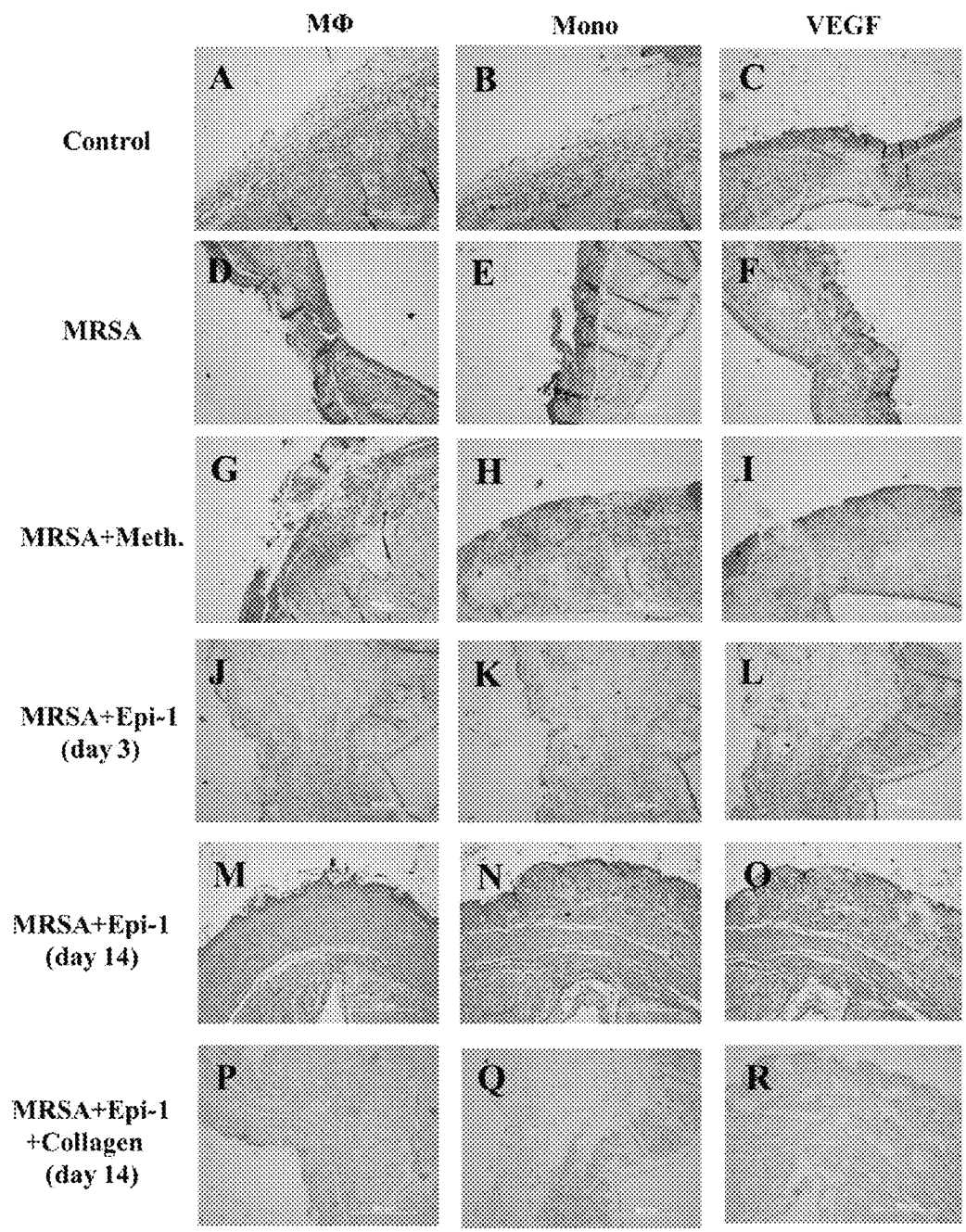
FIG. 7 shows that Epi-1 regulated the recruitment of monocytes and macrophages, and VEGF production in infected wounds; wherein a skin region of about 1 square centimeter was removed from the abdomen of non-anaesthetized mice, and the wound was infected with 50 µl of broth mix containing $10^6$ cfu of MRSA alone, or together with methicillin, Epi-1, or Epi-1 with collagen; and skin samples from the injured area were fixed and subjected to staining with antibodies against monocytes, macrophages, and VEGF at 3 days post-treatment.

During wound healing, monocytes begin to replace neutrophils at 48 hours, in order to remove wound debris; this is followed by the proliferation phase at 72 hours, during which time several growth factors are induced. Tissue sections from the wounded area were subjected to Giemsa staining to reveal monocytes (pale blue), lymphocytes (dark blue), and erythrocytes (pink) (see FIGS. 6A-6F). Untreated sections exhibited excessive accumulation of monocytes (FIGS. 6A-6C), while Epi-1 treatment reduced their recruitment (FIGS. 6D-6F). Production of VEGF is stimulated during wound healing, and is important for provision of the oxygen, nutrients, and immune cells required for antibacterial activity and wound healing. To confirm whether production of this protein is also affected by Epi-1, skin sections were stained and probed with specific antibodies against monocytes, macrophages, and VEGF. While staining against monocytes, macrophages, and VEGF was prominent in MRSA-infected sections (FIGS. 7A-7I), it was clearly reduced by treatment with Epi-1 (FIGS. 7J-7R).

Example 5

Effect of GE33 on Wound Closure

Figure 8A:
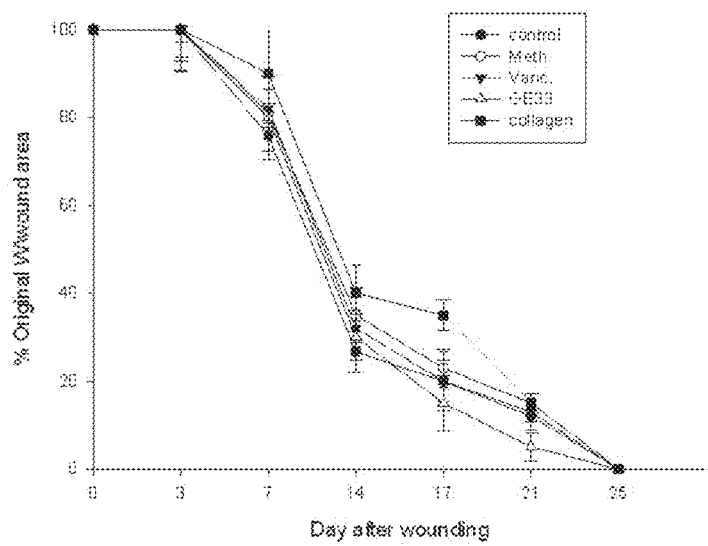
FIGS. 8A-8D show the closure of clean and contaminated wounds treated with GE33; wherein the areas of full thickness wounds (initially 1.5 cm in diameter) were measured from the time of wounding until closure.
Figure 8B:
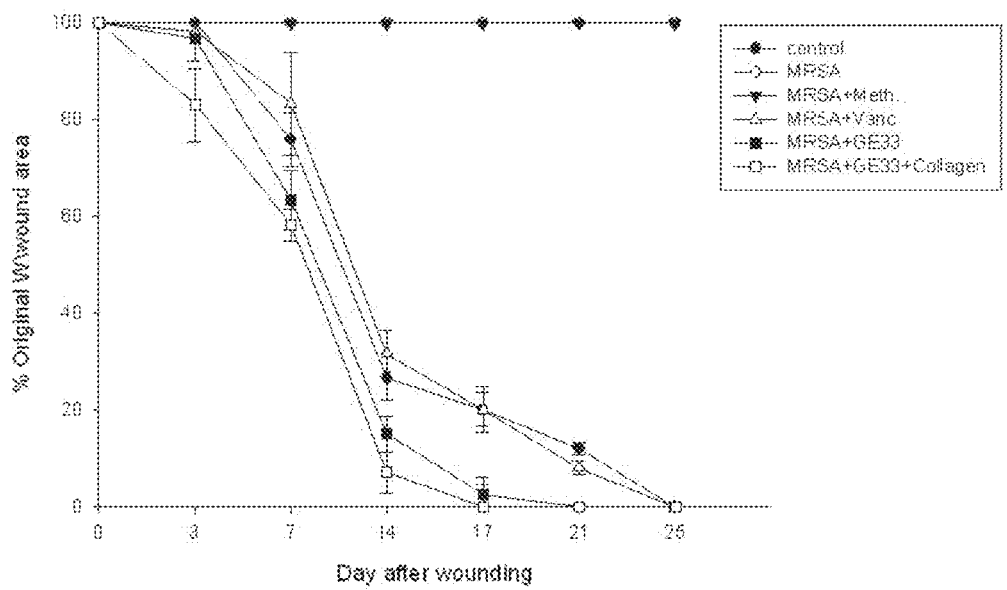
Figures 8C, 8D:
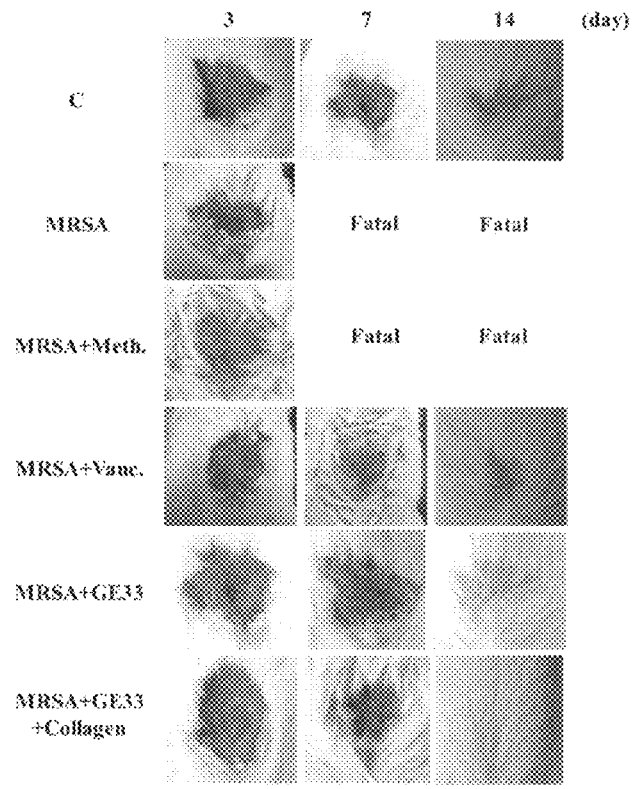

The mice were treated with GE33 and collagen, in place of Epi-1 in the previous examples. As shown in FIG. 8A, GE33 promoted the wound healing. No statistical difference was found between the areas of untreated wounds and Tegaderm™ or antibiotic-treated wounds, with all closing at Day 21~25, which was not unexpected, as skin wounds heal efficiently in healthy young mice, and it is unlikely that this process can be significantly improved. However, it was found that the untreated infected wounds resulted in death in the first week (FIG. 8B). Treatment with vancomycin resulted in a similar wound closure time to the control, while wound closure was accelerated by treatment with GE33 alone or together with collagen. Such an increase in wound closure was not observed in uncontaminated wounds, suggesting that GE33 and collagen may facilitate wound recovery by combating infection. Unlike the uncontaminated wounds, wound size was largely unchanged after one week in all treatment groups (FIG. 8B). By 14 days, wound size in the GE33-treated group was smaller than that of the vancomycin-treated group ($P<0.05$). However, both groups demonstrated full closure by the end of Day 25 (FIG. 8C).

The increase in wound size in untreated contaminated wounds, and the lack of closure in the MRSA and MRSA+Meth (methicillin) treatment groups (FIG. 8B) suggested active wound infection. This was supported by quantitative assessment of the wound flora (FIG. 8D), showing that the initial inoculum of approximately $10^4$ cfu/10 µl of each organism increased to about $10^8$ cfu/10 µl in the MRSA and MRSA+Meth groups at Day 3; between Days 7 and 17, the colony counts in the MRSA+Vanc, MRSA+GE33, and MRSA+GE33+collagen groups decreased, with the most rapid decrease being observed in the GE33 group (significantly different as compared to the other groups at Day 14).

Example 6

Effect of GE33 on Dermal and Epidermal Maturation

Figure 9A:
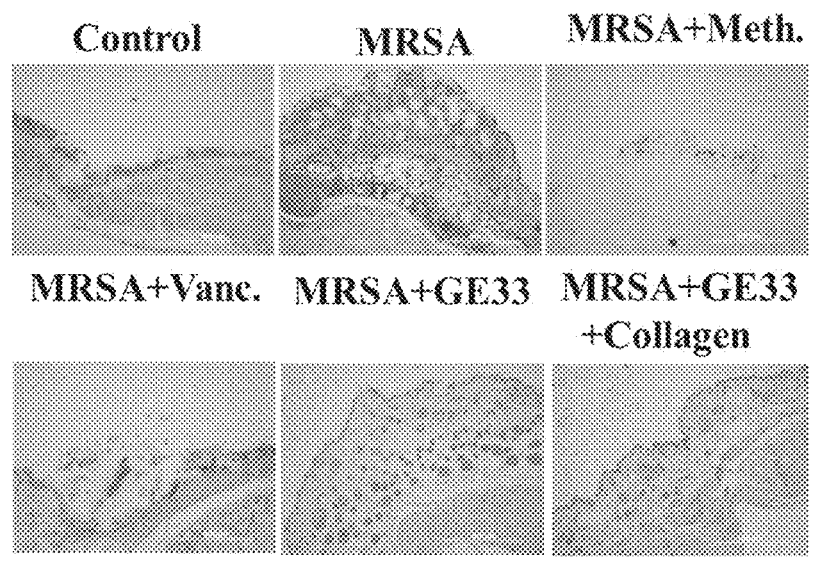
FIGS. 9A-9B provide the results of the evaluation of wounds and skin maturation by Gram staining of tissues.

In clinical practice, attempts to count MRSA colonies through culturing anaerobes from skin wounds often result in underestimates, due to the aerobic nature of the site. The wounds were evaluated using Gram staining of tissues, to determine if anaerobes on the skin exceeded the counts achieved by quantitation of aerobes (FIG. 9A). Quantitation of the number of Gram-positive organisms per high-power field in the upper dermis reflected the quantitative cell counts. As expected, bacterial loads were reduced more quickly upon treatment with the antimicrobial agents.

Figure 9B:
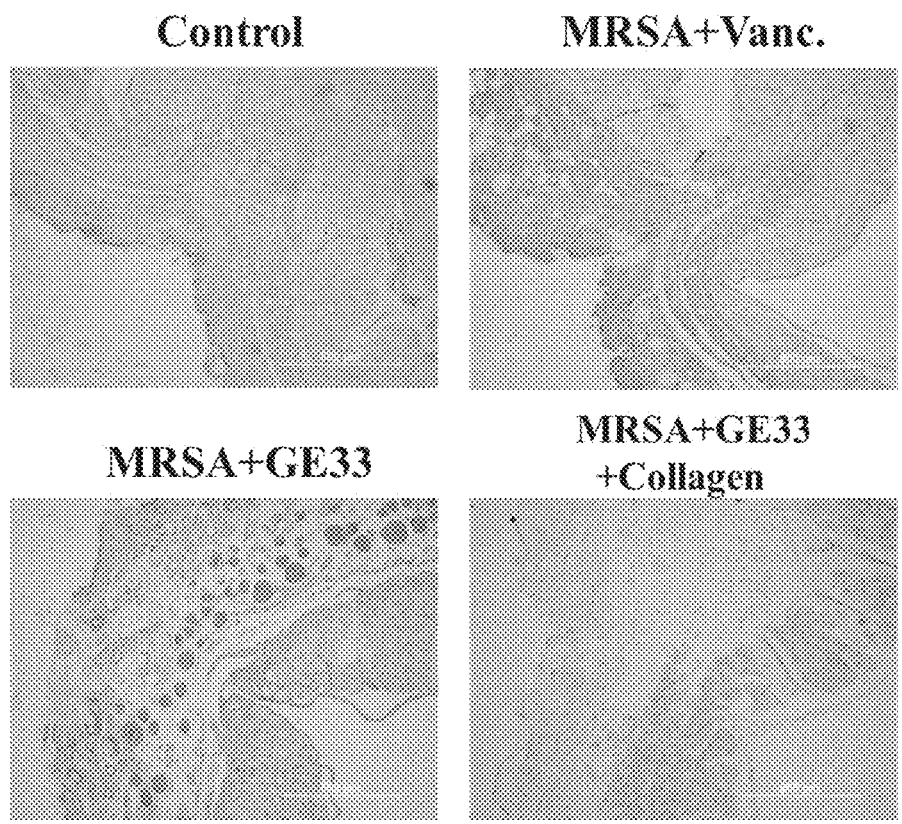

The above data demonstrating enhanced wound closure suggest that treatment with GE33 alone or together with collagen facilitate maturation of the dermal matrix. We examined this via routine histological analyses (FIG. 9B). Dermal maturation is normally assessed at the proliferation, remodeling, and maturation stages. Wounds treated with GE33-incorporated collagen exhibited accelerated progression at all three of these stages. Accelerated healing was also noted in the epidermal compartment (FIG. 9B). Epithelialization was initiated by day 7 in wounds treated with GE33 alone or together with collagen, but not in control or antibiotic-treated wounds. Wounds treated with GE33 and GE33-incorporated collagen were multilayered as in normal skin, and fully mature by day 21. Keratinization and regeneration of the epithelium showed no signs of irregularity, whereas wounds treated with Tegaderm™ and MRSA+Vanc displayed impairment in overall epidermal maturation as compared to the GE33 group. It was concluded that GE33 hd anti-bacterial activity against MRSA in vitro.

Example 7

Evaluation of Antimicrobial Activity for GE33

Figure 10A:
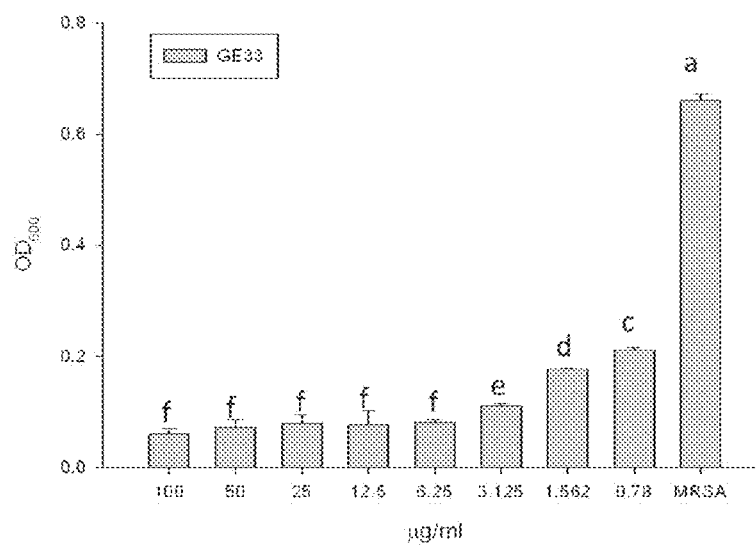
FIGS. 10A-10B show the antibacterial and immune modulatory functions of GE33; wherein FIG. 10A provides the activities of the indicated concentrations of GE33 against MRSA.
Figure 10B:
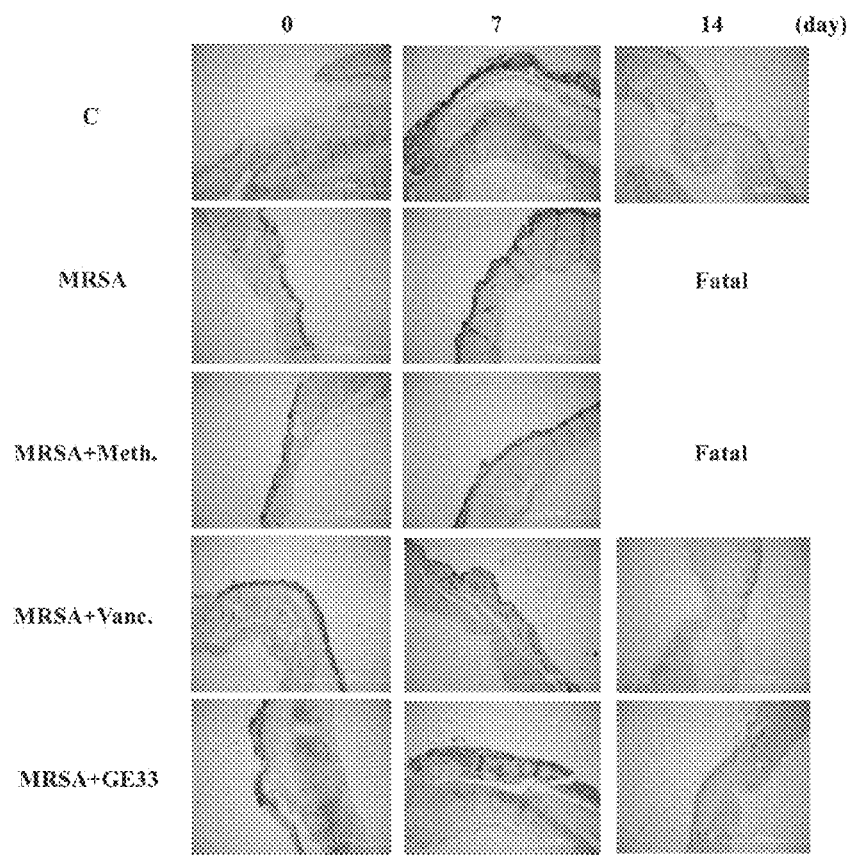

As shown in FIG. 10A, the minimal inhibitory concentration (MIC) for GE33 was >6.25 mg/L against MRSA. Similarly, >6.25 mg/L of GE33 effectively killed MRSA suspended in 10 mM sodium phosphate buffer, pH 7.2, suggesting that the optimal dose of GE33 for treating MRSA was 6.25 mg/L. The effect of GE33 in promotion of the innate immune response and cytokine production were evaluated after the wound healing in infected mice. Giemsa staining revealed accumulation of immune cells in the skin of infected mice treated with MRSA (FIG. 10B).

Figure 11:
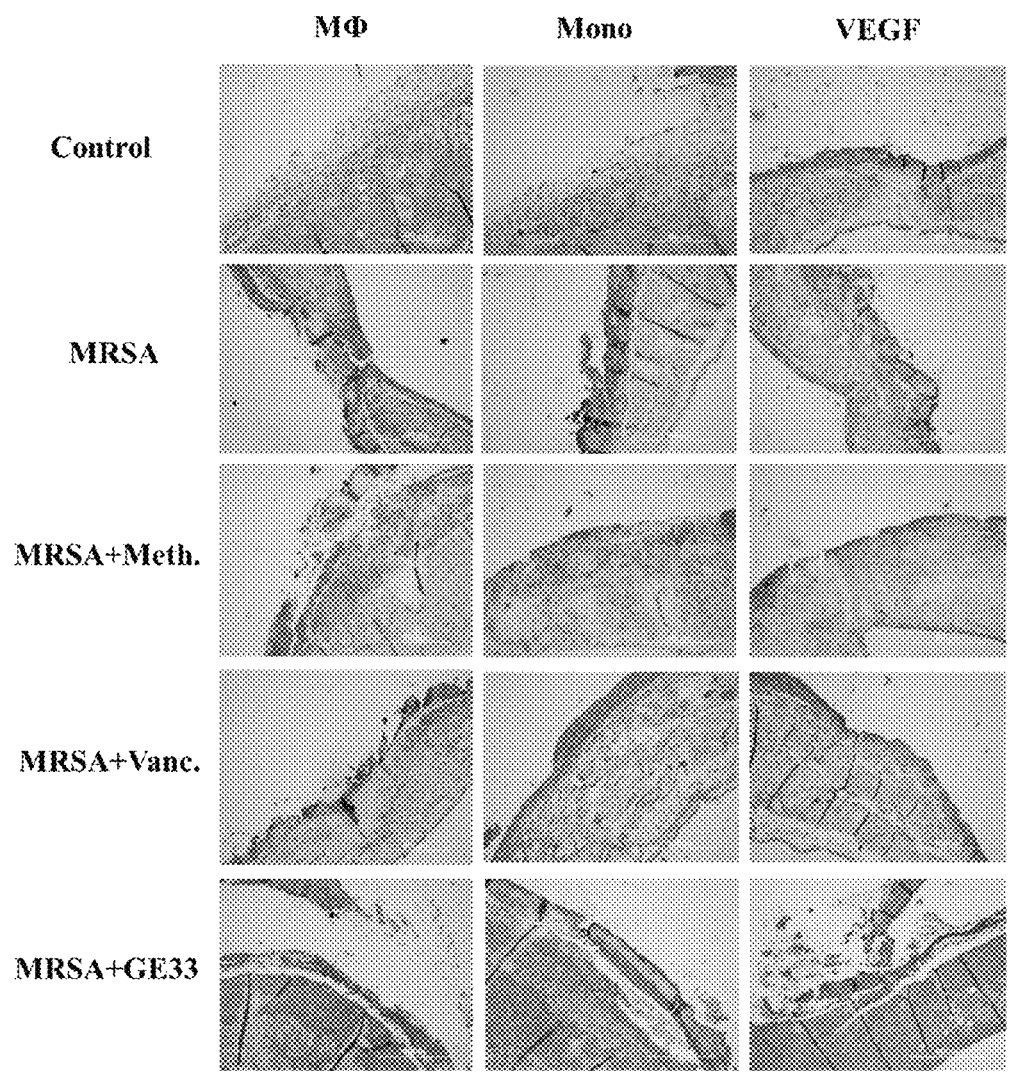
FIG. 11 shows that the treatment of the infected mice with GE33 enhanced infiltration of macrophages and monocytes, and increased VEGF; wherein the mice were sacrificed at Day 3; and cryosections of wound sites were fixed in formaldehyde, and immunohistochemical analysis was performed using specific antibodies against macrophages (MΦ), monocytes (Mono), or VEGF, as indicated. (r=3; n=3).

Further, the mechanism underlying the direct antimicrobial activity of GE33 was established. The ability of GE33 to modulate the immune cells of mice was measured using IHC. As shown in FIG. 11, the IHC with cell surface marker antibodies revealed a significant increase in the infiltration of monocytes and macrophages in infected wounds treated with GE33 or GE33-incorporated collagen. In addition, proliferation-associated VEGF was increased in these groups (FIG. 11).

Figure 12A:
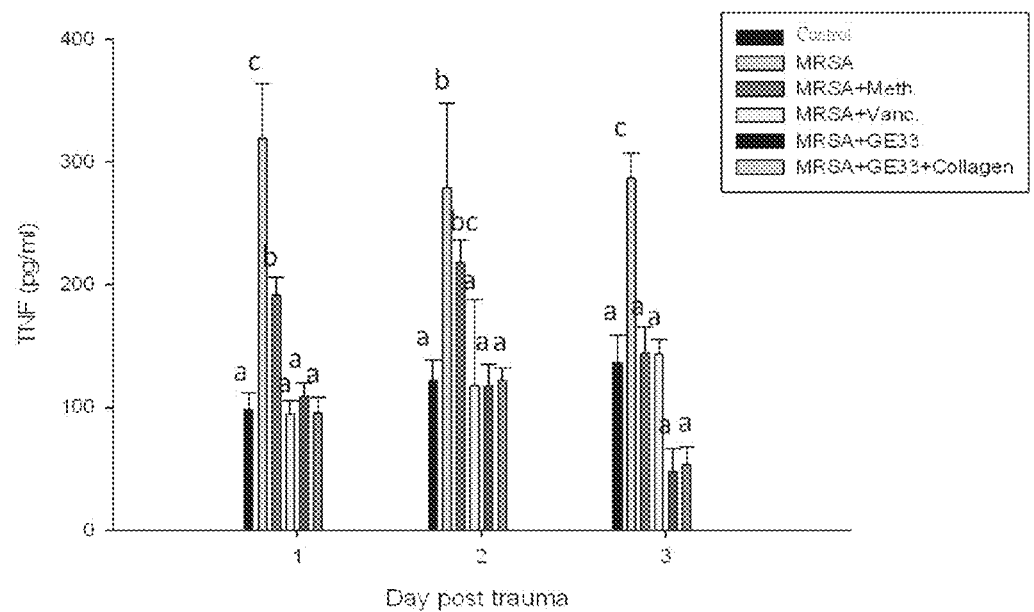
FIGS. 12A-12C show that the treatment of MRSA-infected mice with GE33 decreased the release of MCP-1, IL-6, and TNF; and the mice were treated with GE33 after infection of wounds with MRSA, and cytokine secretion was measured by ELISA, the results of TNF are shown in FIG. 12A, IL-6 in FIG. 12B and MCP-1 in FIG. 12C (r>3; n=3; values with different letters show significant differences ($p<0.05$), as determined by ANOVA).
Figure 12B:
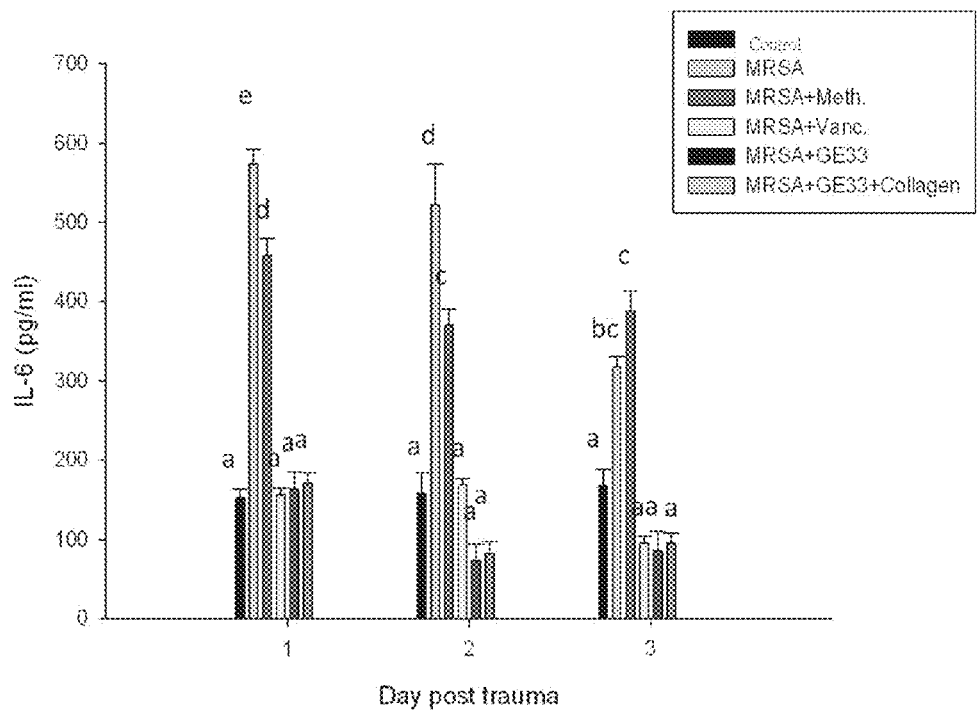
Figure 12C:
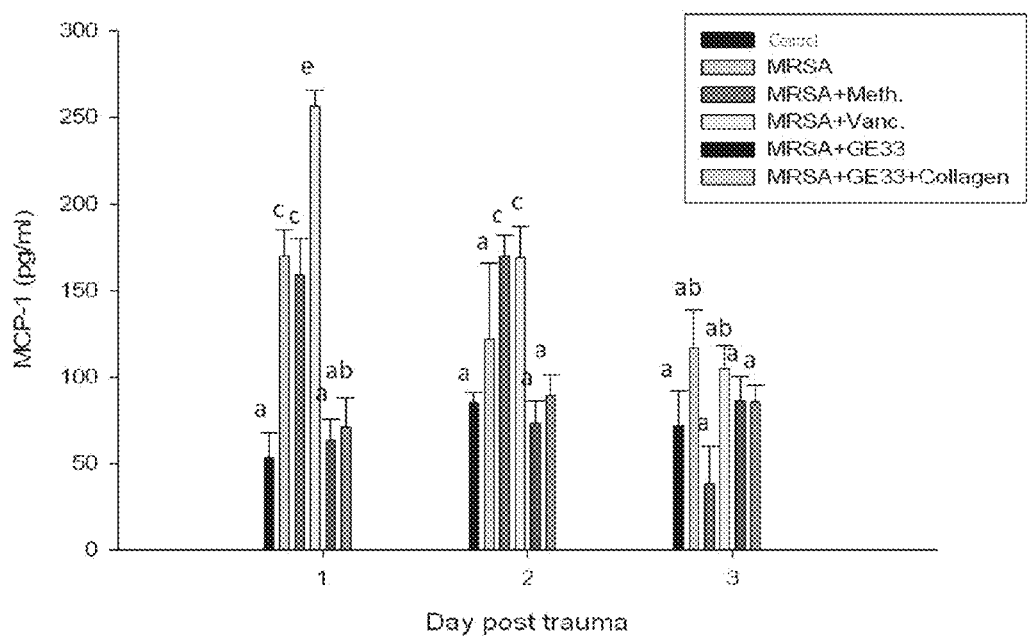

The pro-inflammatory cytokine IL-6 acts as a potent modulator of innate immunity, while the chemokine MCP-1 enhanced the recruitment of monocytes and macrophages to tissue surrounding wounds. Serum chemokine and cytokine levels in MRSA-infected mice were measured at Day 3 after treatment. The MRSA-infected mice were used as a positive control to confirm cytokine activation. The GE33 treatment decreased induction of MCP-1, IL-6, and TNF as compared to the positive controls (FIG. 12).

It was concluded that either Epi-1 or GE33 Epi-1 is a potential complementary treatment to the use of antibiotics, which is compatible with the use of antibiotics but without any apparent immunotoxic effects.

The descriptions and claims as provided should be understood as of demonstrative purpose instead of limitative in any way to the scope of the present invention.

We claim:

1. A method for preventing and treating MRSA infection in a burn wound comprising:
applying to the burn wound in a subject in need thereof, a composition comprising Epinecidin-1 (Epi-1) incorporated into collagen at a therapeutically effective amount to heal the burn wound, together with a pharmaceutically acceptable carrier, and
wherein Epi-1 consists of a peptide having the full length of the amino acid sequence of SEQ ID NO: 1.

2. The method according to claim 1, wherein the composition ameliorates excess recruitment of monocytes and macrophage cells, increases VEGF expression, and decreases immune responses.

* * * * *

SEQUENCE LISTING

<160> NUMBER OF SEQ ID NOS: 2

<210> SEQ ID NO 1
<211> LENGTH: 21
<212> TYPE: PRT
<213> ORGANISM: grouper

<400> SEQUENCE: 1

Gly Phe Ile Phe His Ile Ile Lys Gly Leu Phe His Ala Gly Lys Met
1               5                   10                  15

Ile His Gly Leu Val
            20

<210> SEQ ID NO 2
<211> LENGTH: 33
<212> TYPE: PRT
<213> ORGANISM: Pardachirus marmoratus/pavoinus

<400> SEQUENCE: 2

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Gly Gln
            20                  25                  30

Glu